(12) United States Patent
Woolf et al.

(10) Patent No.: US 8,835,160 B2
(45) Date of Patent: Sep. 16, 2014

(54) SYNTHETIC BIOLOGY VECTORS

(75) Inventors: Peter Woolf, Ann Arbor, MI (US); Alex Ninfa, Brighton, MI (US); Avraham E. Mayo, Ann Arbor, MI (US); Steven Selinsky, Ann Arbor, MI (US); Qi Xiu Song, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1540 days.

(21) Appl. No.: 11/935,164

(22) Filed: Nov. 5, 2007

(65) Prior Publication Data
US 2009/0061520 A1  Mar. 5, 2009

Related U.S. Application Data

(60) Provisional application No. 60/856,461, filed on Nov. 3, 2006.

(51) Int. Cl.
*C12N 15/63* (2006.01)

(52) U.S. Cl.
USPC .................. 435/320.1; 435/325; 435/252.3

(58) Field of Classification Search
None
See application file for complete search history.

(56) References Cited

U.S. PATENT DOCUMENTS

| 5,464,764 A * | 11/1995 | Capecchi et al. ............... 435/6 |
| 6,576,443 B2 * | 6/2003 | Hennecke et al. ............ 435/69.1 |
| 6,897,020 B2 * | 5/2005 | Link et al. ...................... 435/6 |

OTHER PUBLICATIONS

Microbial Genetics Glossary Definition for "selectable marker" obtained Online Mar. 25, 2011.*
Wiess et al., "Genetic Circuit Building Blocks for Cellular Computation, Communications, and Signal Processing" 2002, Natural Computing, Kluwer Academic Publishers, p. 1-40.
Yokobayashi et al., "Directed evolution of a genetic circuit" 2002, Proc. Natl. Acad. Sci. 99:16587-91.

* cited by examiner

*Primary Examiner* — Catherine Hibbert
(74) *Attorney, Agent, or Firm* — Casimir Jones, S.C.

(57) ABSTRACT

The present invention provides compositions, methods and kits for generating synthetic genetic circuits in biological systems. In particular, the present invention provides vectors, reagents and methods of their use in constructing synthetic genetic circuits in bacteria.

1 Claim, 8 Drawing Sheets

Initial strain:

Step 1

Step 2

Step 3

Step 4

Initial strain:

Step 1

Step 2

Step 3

Step 4

FIGURE 8

SYNTHETIC BIOLOGY VECTORS

The present application claims priority to U.S. Provisional Application No. 60/856,461, filed on Nov. 3, 2006, incorporated herein by reference in its entirety.

FIELD OF THE INVENTION

The present invention provides compositions, methods and kits for generating synthetic genetic circuits in biological systems. In particular, the present invention provides vectors, reagents and methods of their use in constructing synthetic genetic circuits in bacteria.

BACKGROUND OF THE INVENTION

Classical genetic engineering with recombinant DNA is a powerful and widespread technology that enables scientists to redesign life forms by modifying or extending their DNA. Advances in this field allow us to gain insight into the operational principles that govern living organisms. This insight can be applied to a variety of fields, for example human therapeutics, synthesis of pharmaceutical drugs and other products, molecular fabrication of biomaterials, crops and livestock engineering, and toxin detection with biological sentinels (Weiss et al., 2002, Natural Computing, Kluwer Academic Publishers, p. 1-40).

A newly emerging field of synthetic genetics studies the theoretical and experimental design of simple synthetic genetic circuits to aid in elucidating the operating principles of more complex genetic regulatory networks in living cells. This type of genetic and biological engineering will have a great impact in controlling cellular behaviors for biotechnology and human therapeutics. Unfortunately, biology is such that it is difficult to predict the precise behavior of even the simplest synthetic network. Currently, directed evolution has been applied to the creation of synthetic genetic circuits (Yokobayashi et al., 2002, Proc. Natl. Acad. Sci. 99:16587-91) by random mutagenesis, however the process is time consuming and requires multiple rounds of mutagenesis and selection of plasmid colonies for desired mutants. Weiss 2002 also described several methods for building genetic circuits. The BioBricks Foundation is an organization founded by engineers and scientists from MIT, Harvard, and UCSF where scientists development the use of technologies based on Bio-Bricks, which are standard DNA parts that encode basic biological functions. Using BioBricks, a synthetic biologist or biological engineer can, to some extent, program living organisms in the same way a computer scientist can program a computer. However, tools are needed to apply this technology and make it more available.

Therefore, what are needed are foundational technologies that make engineering biology routine and advance the field of biological engineering so that its full potential can be realized, which could lead to significant advances in the medical and pharmaceutical sciences for developing therapies and drugs for human diseases.

SUMMARY OF THE INVENTION

The present invention provides compositions, methods and kits for generating synthetic genetic circuits in biological systems. In particular, the present invention provides vectors and reagents and methods of their use in constructing synthetic genetic circuits in bacteria.

In some embodiments, the present invention provides methods for creating a synthetic genetic circuit comprising: a) providing: i) a host cell, ii) a first vector wherein the first vector comprises a selectable marker sequence and wherein the vector is stably integrated into the host cell genome, iii) a second vector comprising a different selectable marker sequence, genetic elements of interest, and first and second homologous sequence that are each homologous to a portion of the selectable marker sequence in the first vector, wherein the first homologous sequence is located 3' of the different selectable marker sequence and the genetic elements of interest, and the second homologous sequence is located 5' of the different selectable marker sequence and the genetic elements of interest, and b) applying the second vector to the host cell such that recombination occurs between the selectable marker sequence in the first vector and the first and second homologous sequences thereby causing insertion of the different selectable marker sequence and the genetic elements of interest at a location within the selectable marker sequence of the host cell's genome, thereby generating a synthetic genetic circuit. In particular embodiments, the present invention provides said host cell with said synthetic genetic circuit.

In certain embodiments, the methods further comprise providing a third vector comprising: i) an additional selectable marker sequence that is not the same as the different selectable marker sequence on the second vector; ii) genetic elements of interest, and iii) third and fourth homologous sequences that are each homologous to a portion of the different selectable marker sequence in the second vector, wherein the third homologous sequence is located 3' of the additional selectable marker sequence and the genetic elements of interest, and the fourth homologous sequence is located 5' of the additional selectable marker sequence and the genetic elements of interest, and step c) applying the third vector to the host cell such that recombination occurs between the different selectable marker sequence in the second vector and the third and fourth homologous sequences thereby causing insertion of the additional selectable marker sequence and the genetic elements of interest at a location within the different selectable marker sequence of the host cell's genome.

In further embodiments, the present invention provides systems comprising: a) a first vector wherein the first vector comprises a selectable marker sequence; and b) a second vector comprising a different selectable marker sequence, genetic elements of interest, and first and second homologous sequence that are each homologous to a portion of the selectable marker sequence in the first vector, wherein the first homologous sequence is located 3' of the different selectable marker sequence and the genetic elements of interest, and the second homologous sequence is located 5' of the different selectable marker sequence and the genetic elements of interest.

The vectors and methods of the present application can be used to permanently incorporate genetic elements into a chromosome, for example into a bacterial chromosome. Most methods for modifying bacteria rely on the expression of genes from plasmids in the cytosol. For genetic systems, these plasmids have the disadvantage that they are present in variable number, and as such preclude tight regulation of the dynamics of protein expression.

Current genetic construction methods require the addition of all of genetic programs at a single time. This mode of construction problem generally precludes large genetic programs due to size constraints in the host and also makes troubleshooting extremely difficult. The vectors described herein overcome this problem by furnishing novel recursive "landing pad structures". In some embodiments, using vectors and transformation methods of the present invention, recombination of genetic material into the biological system, for example bacteria, first takes place in a non-essential gene in the chromosome. Bacteria containing the newly incorporated genetic material are selected for by a drug resistance gene (A) (e.g., ampicillin, kanamycin) contained in the vector, which only allows those bacteria with drug resistance gene (A) to survive. In the next round of bacterial transformation, recombination occurs directly into the drug resistance gene (A) with an additional genetic component and a new drug resistance gene (B) that is different from (A). The present invention is not limited to a particular mechanism. Indeed, an understanding of the mechanism is not necessary to practice the present invention. Nonetheless, it is contemplated that by repeatedly (i.e., recursively) incorporating new genetic material and associated drug resistance genes into the biological system, for example bacteria, incremental building and testing of complex genetic circuits occurs. The present invention is not limited to bacteria, indeed other biological systems are also contemplated for use with compositions and methods of the present invention. For example, the recursive incorporation of new genetic material and associated drug resistance genes using compositions and methods of the present invention are equally amenable to mammalian, yeast, algae and plant biological systems.

In some embodiments, the vectors of the present invention also include novel "DNA barcodes" that are used to uniquely characterize the DNA insertion by the polymerase chain reaction (PCR) or other techniques. The addition of DNA barcodes frees the user from having to sequence the biological genome at every step for verification of insert incorporation, thereby saving both time and money.

It is contemplated that the compositions and methods as described herein will greatly accelerate the field of synthetic biology by providing vectors for creating stable and testable genetic programs in biological systems that are easy to use and more time and cost efficient.

In some embodiments, the present invention provides methods for creating synthetic genetic circuits in a biological system comprising providing a host cell and two vectors, wherein the first vector comprises a target nucleic acid that is homologous to sequences found in the host cell, genetic elements of interest, and a first antibiotic resistance gene, and wherein the second vector comprises additional genetic elements, the first antibiotic resistance gene rendered into two parts flanking the additional genetic elements and a second antibiotic resistance gene, contacting the first vector with the host cell wherein the first vector is incorporated into the host cell genome, and contacting the second vector with the host cell wherein the second vector is incorporated into the modified host cell thereby creating a synthetic genetic circuit in the host cell. In some embodiments, the genetic elements of interest comprise nucleic acid sequences that encode proteins of interest. In some embodiments, the vectors further comprise a bar code that allows for screening for the incorporation of the synthetic genetic circuit into the host cell. The host cell can either be a prokaryotic or eukaryotic cell.

The present invention provides, in some embodiments, vector systems for creating a synthetic genetic circuit comprising two vectors, wherein the first cell comprises a target nucleic acid that is homologous to sequences found in the host cell, genetic elements of interest, and a first antibiotic resistance gene, and wherein the second vector comprises additional genetic elements, the first antibiotic resistance gene rendered into two parts flanking the additional genetic elements and a second antibiotic resistance gene. In some embodiments, at least one of the vectors in the vector system further comprises a bar code as described herein. In some embodiments, the genetic elements of the vectors in the vector system are genes that encode for desired proteins of interest.

In some embodiments, the present invention provides host cells comprising the vector system as described above, those host cells being either prokaryotic and/or eukaryotic host cells.

In some embodiments, the present invention provides kits or systems for providing an investigator the tools to practice the methods of the present invention. For example, kits of the present invention comprise initial vectors for creating the vectors of the present invention, and instruction on how to create the vectors and use them in host cells. In some embodiments, the initial vectors comprise bar code sequences. In some embodiments, the kits comprise reagents, buffers, and the like for creating the vectors and/or performing the methods of the present invention. In other embodiments, the kits further comprise host cells, either one or both of prokaryotic and eukaryotic host cells.

DESCRIPTION OF THE FIGURES

FIG. 4 shows an exemplary set of four vectors created using pUMSB1. T=target gene sequence, AB0=β-lactamase gene, AB1=antiobiotic resistance gene 1, AB2=antibiotic resistance gene 2, bars represent RE sites, P1-4=promoter sequences for gene of interest, lollypops represent termination sequences, and dumbbells represent bar codes for screening of insert.

DEFINITIONS

As used herein, a "genetic program" of a biological system, like a cell, refers to a physiological change brought about by a temporal pattern of activation of a particular subset of genes. "Genetic circuits" made of "genetic elements" can modulate physiological change, as they are made of a subset of genes and associated nucleic acid elements such as promoter, enhancers, and other nucleic acid sequences that impact the expression of a gene.

As used herein, the term "homologous recombination target sequences" refers to nucleic acid sequences that provide recognition sequences for recombination factors and the location where recombination takes place.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "transgene" as used herein refers to a foreign gene that is placed into an organism by, for example, introducing the foreign gene into a bacterial cell. The term "foreign gene" refers to any nucleic acid (e.g., gene sequence) that is introduced into the genome of an organism by experimental manipulations and may include gene sequences found in that organism (e.g., endogenous genes) or gene sequences that are foreign to that organism (e.g., exogenous genes).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "regulatory element" refers to a genetic element that controls some aspect of the expression of nucleic acid sequences. For example, a promoter is a regulatory element that facilitates the initiation of transcription of an operably linked coding region.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal. A host cell of the present invention accommodates the vectors of the present invention and is used in methods of the present invention as described herein.

DETAILED DESCRIPTION OF THE INVENTION

The incorporation of genetic material into a cell's genome is typically performed by cloning all the desired nucleic acids to be incorporated into one vector followed by transformation of the host cell in such a fashion that the genetic material of interest is incorporated stably into the host cell genome. It is more or less a one shot affair, wherein if more than one gene needs to be incorporated then the vector typically comprises multiple promoters and/or transcriptional elements, all of which are inserted at one time, or multiple complete vectors are all incorporated into the same host cell. The problem with such methods is that large vectors carrying multiple genetic elements for insertion into a host genome are tremendously difficult to work with; for example, the vectors themselves can undergo recombination within the vector thereby rearranging the vectors oftentimes results in useless material and an end to an experiment as well as being very difficult to propagate in bacterial or yeast propagation systems. Or, the bulk of the material to be introduced into a cell genome by many large vectors overwhelms the host cell, also leading to the end of an experiment.

The present invention bypasses these difficulties by providing vector compositions and methods for performing multiple rounds of incorporation of genetic material into a host cell's genome in an efficient manner. Multiple genetic elements of interest, for example genes that encode for proteins as well as associated transcriptional and translational elements, as dictated by an investigator, are incorporated in a recursive manner into the same location in a cell's chromosome in a step wise fashion.

A vector as described herein is first incorporated into a host cell genome at a location in a chromosome, preferably a location that is not deleterious to the host cell survival. This incorporated vector serves as the "landing pad" for subsequent incorporation of addition genetic elements into the cell, in a stepwise manner. This landing pad is typically an antibiotic resistance gene, such that selection with the antibiotic yields only those cells which are expressing the desired genetic material of interest. Ensuite, a second vector which comprises a different antibiotic resistance gene from the first, as well as sequences homologous to the first antibiotic resistance gene and additional genetic elements of interest is introduced into the host cell. The second vector, for example, recombines with the first vector via homologous recombination between sequences of the first antibiotic resistance gene (found in both vectors), thereby inserting the new genetic material at a particular location in the genome and allowing for subsequent selection of the newly incorporated genetic elements by virtue of the second, different antibiotic resistance gene. This recursive recombination and selection is exemplified in FIGS. 6 and 8, wherein multiple rounds of combination and selection are depicted.

As such, the present invention provides for recursive incorporation of multiple desired genetic elements (e.g., genes, transcriptional elements, translational elements, etc.) into a host cell genome in a user friendly manner. Such systems allow for the incorporation of multiple elements into a host cell, for example elements that produce proteins thought to be part of a metabolic pathway. The ease of the present invention provides for the testing and experimentation of elements of exemplary metabolic pathways and other biological pathways and systems, such as those important for causing cancer and other diseases, and aids researchers and diagnosticians in studying and defining variables in these, and other, biological systems.

Certain illustrative embodiments of the invention are described below. The present invention is not limited to these embodiments.

The present invention provides vectors for incorporating genetic material into biological systems (e.g., bacteria, yeast, fungi, plants, mammalian, avian, etc.). Vector construction starts with two vectors, examples of which are shown in FIGS. 1 and 2.

Figure 1:
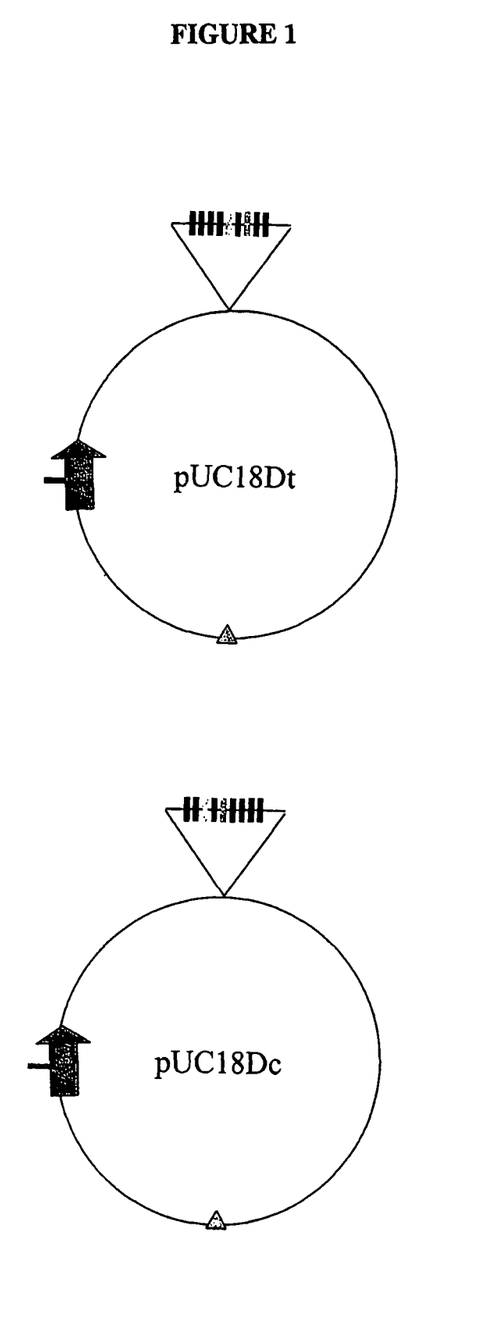
FIG. 1 shows two exemplary pUC18 derivative vectors for use in creating a four-vector system useful in incorporating multiple genetic elements into a host cell genome. The nine bars shown in the MCS of pUC18Dt represent RE sites and include, from left to right, EcoRI (1), SacI (2), NotI (3), NdeI (4), ClaI (5), BamHI (6), SalI (7), XhoI (8), and HindIII (9). For the pUC18Dc vector, the order of the RE sites in the MCS sites is, from left to right, 1, 2, 5, 6, 7, 4, 3, 8 and 9. The "t" in pUC18Dt refers to the insertion of genetic elements in tandem in the MCS on the sense strand, whereas the "c" designation refers to insertion of genetic elements on the antisense strand (converging elements).

In one embodiment, plasmid vectors useful in creating downstream vectors for practicing the present invention, as shown in FIG. 1, are derivative pUC18 backbones wherein the antibiotic selection gene (e.g., ampicillin, kanamycin, etc.) and the lacZ marker gene, if present, are deleted. It is contemplated that the two exemplary vectors in FIG. 1 are used to create a panel of eight vectors (two sets of four vectors). A multiple cloning site (MCS), contemplated to be around, for example, 60-90 bp long such that all nine restriction enzyme (RE) sites described herein are accommodated, is inserted into both vectors pUC18Dt and pUC18Dc. However, the order of the RE sites differs between the vectors as described herein. The difference in order of the RE sites allows for insertion of a variety of genetic elements in varying orientation to facilitate the end user's desired construction. The exemplary RE sites incorporated from left to right in pUC18Dt are EcoRI (1), SacI (2), NotI (3), NdeI (4), ClaI (5), BamHI (6), SalI (7), XhoI (8), and HindIII (9), whereas the order in pUC18Dc is 1, 2, 5, 6, 7, 4, 3, 8 and 9. Incorporation of the MCS and other cloning and creation of vectors is known to those skilled in the art, methods of which can be found in, for example, *Molecular Cloning; A Laboratory Manual*, Sambrook et al., Eds, Cold Spring Harbor Laboratory Press, or *Current Protocols in Molecular Biology*, Ausubel et al., Eds., John Wiley & Sons, incorporated herein in their entireties. An antibiotic resistance gene is incorporated into the vector backbones (AB0), for example, the ampicillin resistance gene β-lactamase (Sutcliffe, 1978, Proc. Natl. Acad. Sci. 75:3737-41) that contains a unique PstI RE site.

Figure 2:
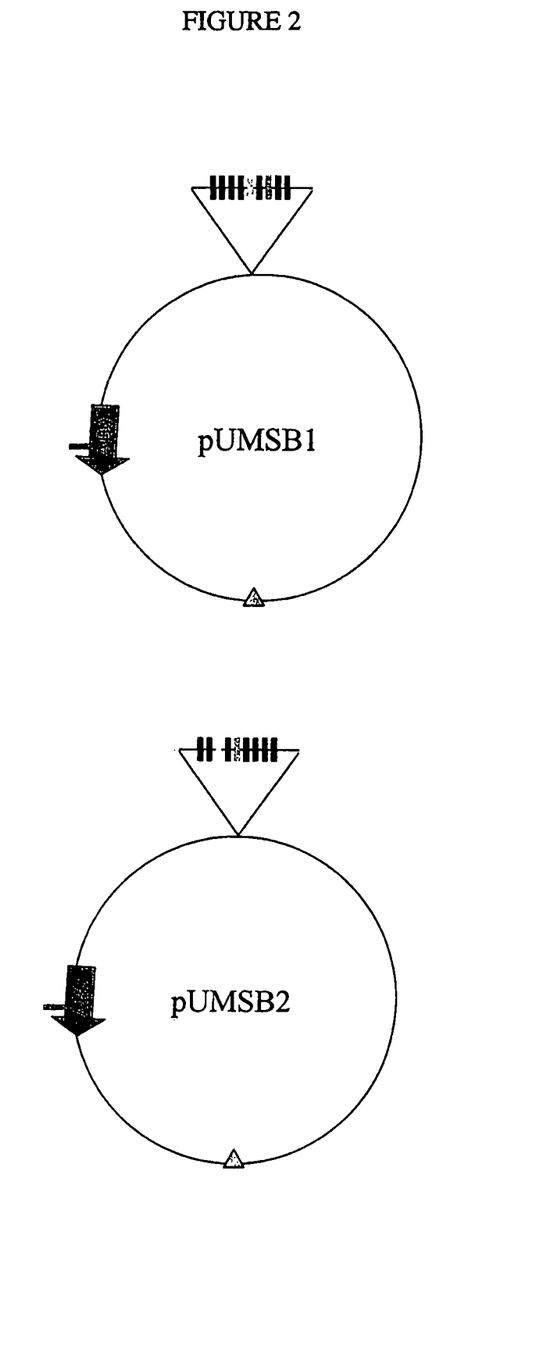
FIG. 2 demonstrates two exemplary pBR322 derivative vectors for use in creating a four-vector system useful in incorporating multiple genetic elements into a host cell genome. The nine bars shown in the MCSs of pUMSB1 and pUMSB2 represent restriction endonuclease (RE) sites and include, from left to right, EcoRI (1), SacI (2), NotI (3), NdeI (4), ClaI (5), BamHI (6), SalI (7), XhoI (8), and HindIII (9).

In another embodiment, the vectors used to create downstream vectors useful for practicing the present invention are derivative pBR322 vectors as seen in FIG. 2 (vectors pUMBS1 and pUMBS2). In some embodiments, the RE sites are cloned into the pUMBS vectors in the same manner, and in the same order, as contemplated for the pUC18D vectors. In some embodiments, the MCS region containing the RE sites replaces the tetracycline resistance gene and the LacZ genes in the pUMBS vectors. In some embodiments, the origin of replication in both the pUC18 and pUMBS vector systems is the same (replicon derived from the plasmid pMB1). One skilled in the art would recognize that any vector system is amenable for use in the compositions and methods of the present invention, and indeed the present invention is not limited by the base vectors used. For example, vectors containing the ColE1 replicon are equally applicable to the vectors, methods and kits of the present invention. The pUC18Dc/pUC18Dc and the pUMSB1 vectors are used as examples in creating recombination vectors as seen in FIGS. 3 and 4, respectively and are not contemplated as limitations of the present invention.

Figure 3:
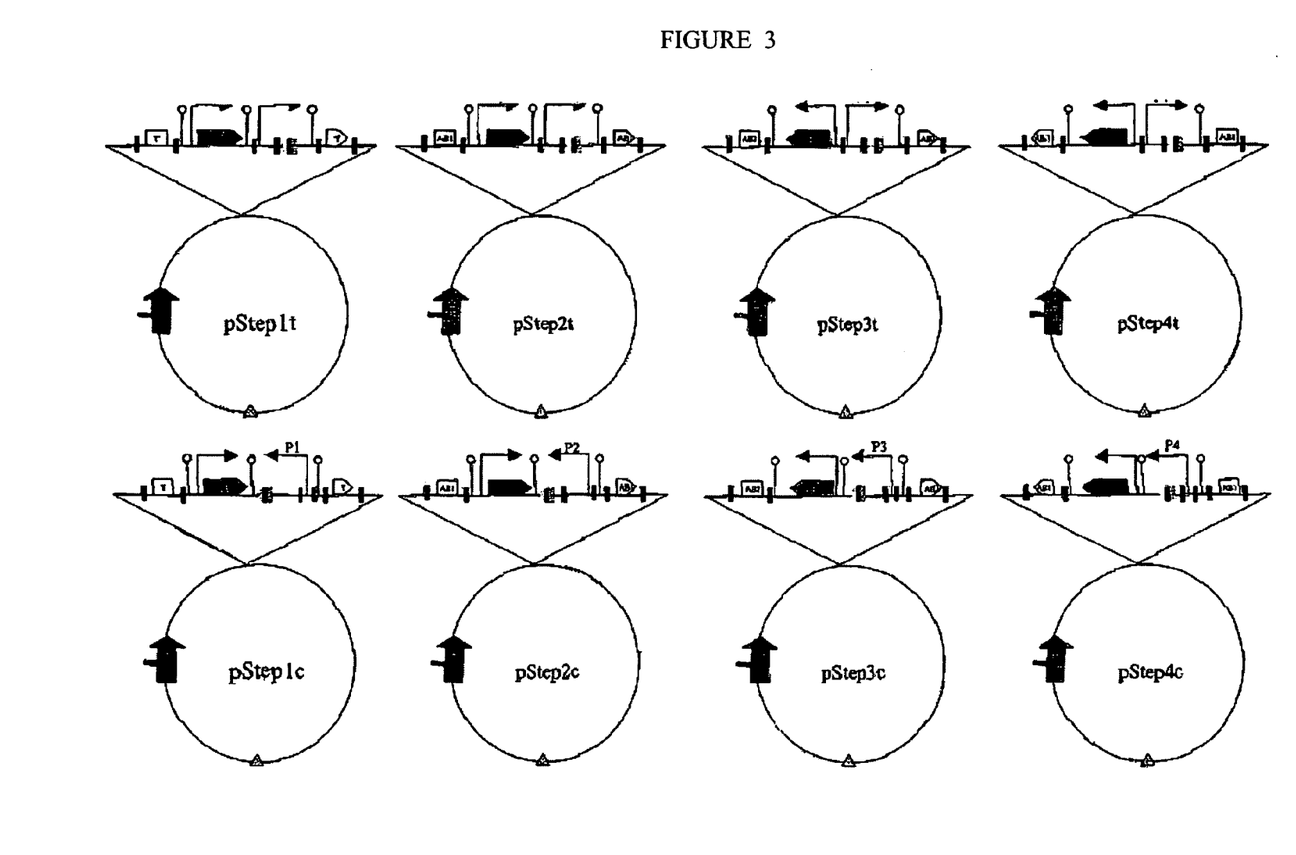
FIG. 3 shows two exemplary vector systems, each with a set of four vectors, that are created using either pUC18Dt or pUC18Dc starting vectors. T=target gene sequence, AB0=β-lactamase gene, AB1=antibiotic resistance gene 1, AB2=antibiotic resistance gene 2, bars represent RE sites, P1-4=promoter sequences for genetic elements of interest, and lollypops represent termination sequences.
Figure 4:
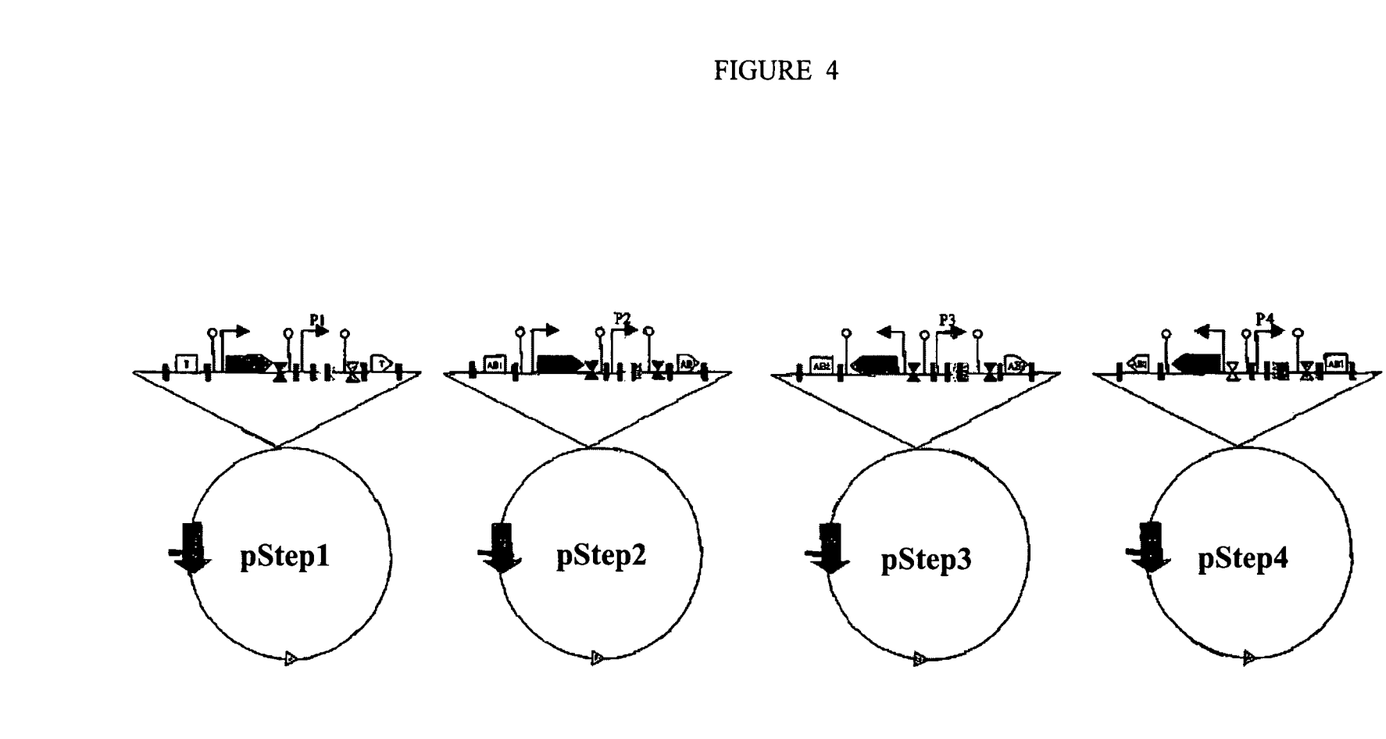

In some embodiments, a set of four different vectors is created using the vectors as previously described (for example, FIGS. 3 and 4). In each of the vectors, a gene of interest is cloned between the NdeI site and one of either ClaI, BamHI or SalI RE sites, as defined by the user (FIG. 3 or 4). The promoter of choice (e.g., bacterial, yeast, fungal, mammalian, plant), designated P1 to P4 is cloned 5' of the genetic element of interest, between the NotI and NdeI RE sites, and may include enhancer elements. The present invention is not limited by the promoter and/or enhancer element used, and any promoter and/or enhancer that transcribes nucleic acid sequences in the target biological system (e.g., bacteria, mammals, plants, etc.) is amenable for incorporation into compositions and methods of the present invention. For example, promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., Science 236: 1237, 1987). Promoters may be tissue specific or cell specific. The term "tissue specific" as it applies to a promoter refers to a promoter that is capable of directing selective expression of a nucleotide sequence of interest to a specific type of tissue (e.g., liver cell, plant parenchyma cell, etc.) in the relative absence of expression of the same nucleotide sequence of interest in a different type of tissue (e.g., brain cell, plant statolith cell). Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic organism. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. Cell type specificity of a promoter may be assessed using methods well known in the art (e.g., immunohistochemical staining).

Promoters may additionally be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue wherein which the promoter is operable. Exemplary promoters include but are not limited to pol III promoters, including promoters from either 7SL signal recognition particle RNA (srpRNA), 5S ribosomal RNA (rRNA), or U6 small nuclear RNA (snRNA) genes as described below, and tRNA, RNase P RNA, and adenovirus VA RNA pol III promoters as described in the following references, which are hereby incorporated in their entirety (Medina, M. F. C. and Joshi, S. (1999) Curr. Opin. Mol. Ther. 1: 580-594; Brummelkamp, T. R. et al.

(2002) Science. 296: 550-553; McManus, M. T. et al. (2002). RNA. 8: 842-850). Promoters may be modified so as to possess different specificity. Examples of pol II promoters are found at the Eukaryotic Promoter Database and as described in Perier et al., 1998, Nucl. Acids Res. 26:353-357 and Perier et al., 2000, Nucl. Acids Res. 28:302-303 and as found on the World Wide Web at epd.isb-sib.ch, incorporated herein by reference in their entireties. For example, cytomegalovirus (CMV), Rous sarcoma virus (RSV), and Simian virus (SV-40) promoter elements all find use in vectors and methods of the present invention.

In contrast, a "regulatable" or "inducible" promoter is one which is capable of directing a level of transcription of an operably linked genetic element of interest in the presence of a stimulus (e.g., heat shock, chemicals, light, etc.) which is different from the level of transcription of the operably linked nucleic acid sequence in the absence of the stimulus. Examples of inducible and/or regulatable promoters include, but are not limited to, tetracycline, ecdysone, heat shock, and GAL1 promoters.

The present invention is not limited by the genetic element of interest. Any nucleic acid sequence is amenable as a genetic element of interest in the present invention. The present invention is also not limited to the source of the genetic element of interest, for example genes from eukaryotic (e.g., mammals, plants, avians, yeast, etc.) and prokaryotic (e.g., bacteria, algae, etc.) systems are contemplated for use with the present invention. Any gene sequence that encodes a protein of interest is amenable for incorporation into the vectors, and useful in the methods, of the present invention. For example, any eukayrotic or prokaryotic genes find use in the present invention, and the present invention is not limited by the gene deemed a "genetic element of interest" of a particular investigator. Genes of interest encode any number of proteins, including but not limited to, enzymes, structural proteins, metabolic proteins, motor activity proteins, and other proteins associated with, for example, biological and/or molecular function. Examples of proteins amendable for use with the present invention can be found at, for example, on the World Wide Web at expasy.org/sprot/.

In some embodiments, for one of the vectors in each set of four (FIG. 3 pStep1t/pStep1c; FIG. 4 pStep1), right and left flanking target sequences (T) for the "landing pad" are cloned between the EcoRI and SacI RE sites, and the XhoI and HindIII RE sites, respectively. The target sequences correspond to sequences in the biological system being used, for example genomic E. coli sequences, and their incorporation into the vectors allows for homologous recombination of the vectors with the genomic DNA at this target site, thereby allowing for incorporation of the vector genetic elements into the host genome. The present invention is not limited by the restriction endonuclease sites used, and any RE sites that fulfill the requirements of the vectors and methods of the present invention are contemplated for use. RE sites are well known to skilled artisans, examples of other RE sites can be found at, for example, at the New England Biolabs, Inc. restriction enzyme site database on the World Wide Web at rebase.neb.com/rebase/rebase.html.

When using the exemplary pUMSB1/2 vectors (FIG. 4), the antibiotic resistance gene (e.g., kanamycin, tetracycline, chloramphenicol, neomycin) and its promoter and terminator sequences are inserted between the NotI and SacI sites. Two different antibiotic resistance genes (AB1 and AB2) are used, alternating between the four vectors, such that an alternation in the antibiotic resistance genes allows for sequential recombination and selection of the incorporated genetic element. The present invention is not limited to the antibiotic resistance genes used, other than the two genes must be different from each other such that alternation in selection is possible. In some embodiments, when using pUC18Dt derived vectors (FIG. 3; pStep1-4t), the antibiotic resistance genes and associated sequences are cloned into the NotI and SacI sites, however for the converging vector set derived from the pUC18Dc vector (FIG. 3; pStep1-4-c), the antibiotic resistance genes and associated sequences are cloned between the SacI site and one of ClaI, BamHI, or SalI RE sites. Additionally, in some embodiments, as the full-length antibiotic resistance gene of choice is cloned for expression as previously described, the alternate resistance gene is cloned in two separate parts, into the EcoRI and SacI sites, and the XhoI and HindIII sites. For example, this arrangement provides for sequential homologous recombination into the antibiotic sites such as that seen with the initial homologous recombination using the target gene sequences of the host.

In some embodiments, a series of unique "bar codes" (designated by hour glass, or bowtie icons in FIG. 4) comprising at least 20 bp nucleic acids per "bar code" are cloned into the vector such that they flank the inserted genetic element. The inserted "bar code" nucleic acid sequences serves as unique locations for verification (e.g., sequencing, PCR) of successful cloning of the genetic element into the vector.

Figure 5:
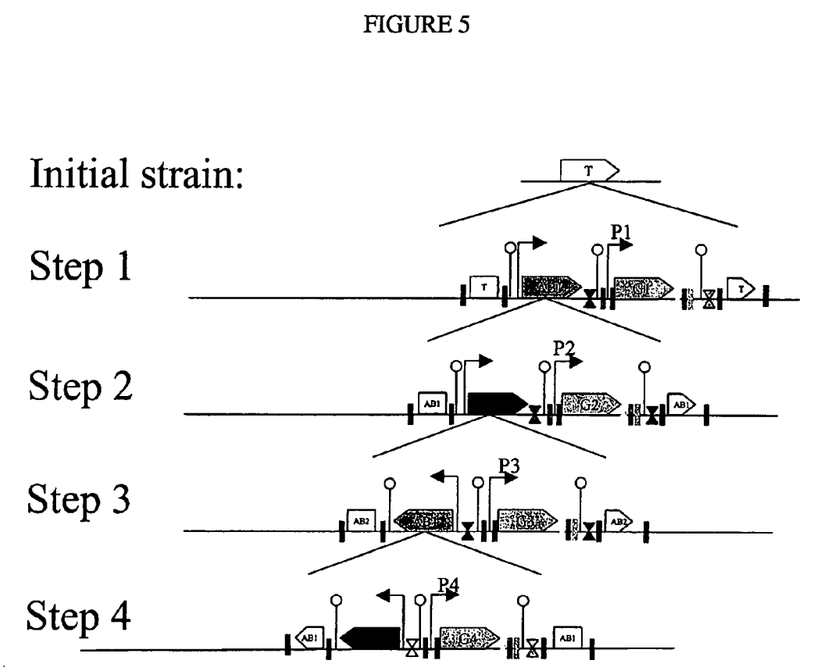
FIG. 5 demonstrates homologous recombination at target (T) sequences and antibiotic genes (AB1 and AB2) when using the pStep1-4 vectors derived from pUMSB1. Initial strain in this example is *E. coli*.
Figure 6:
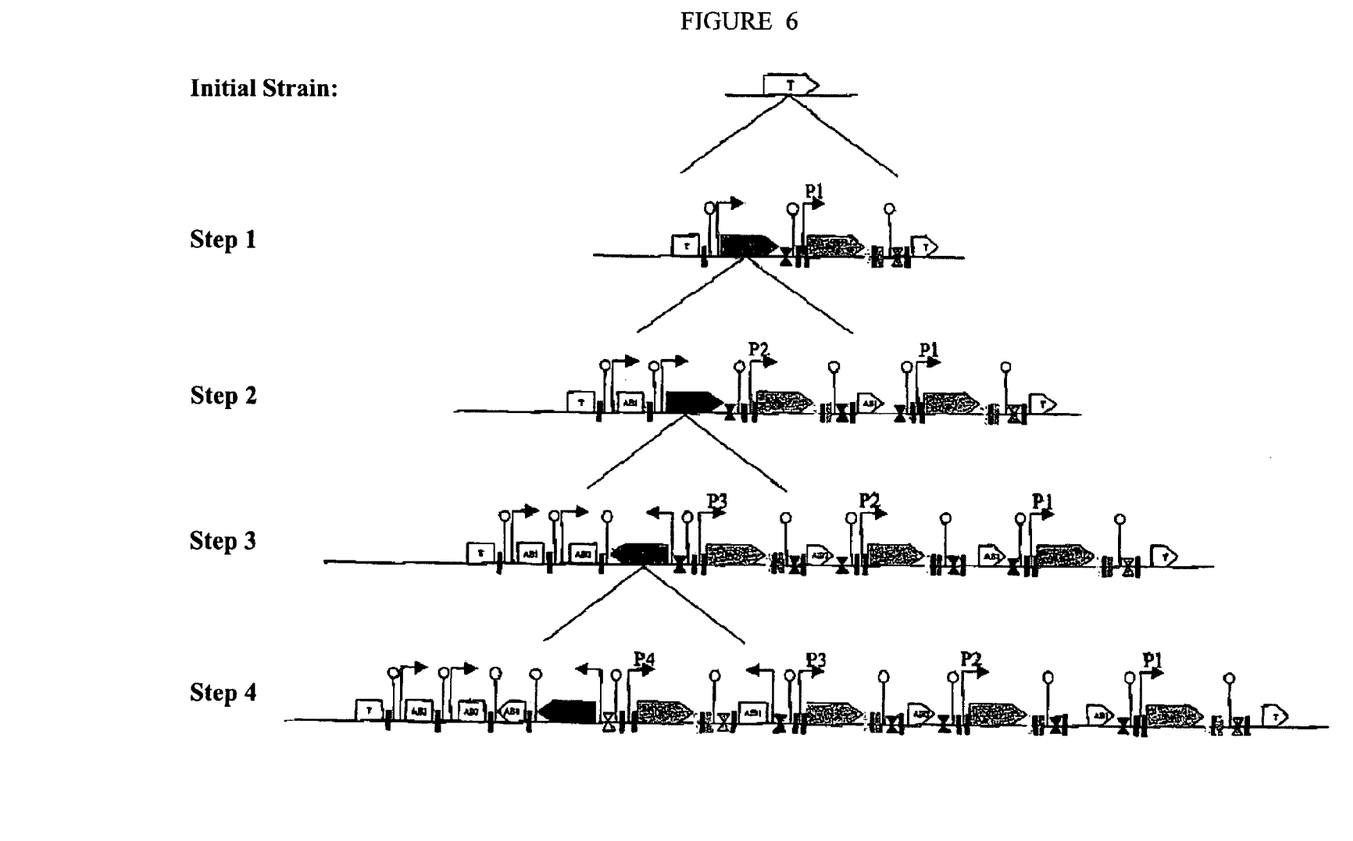
FIG. 6 shows homologous recombination of the four vectors pStep1-4 and their resulting addition of genetic elements into the host genome. The exemplary initial strain in this example is *E. coli*.
Figure 7:
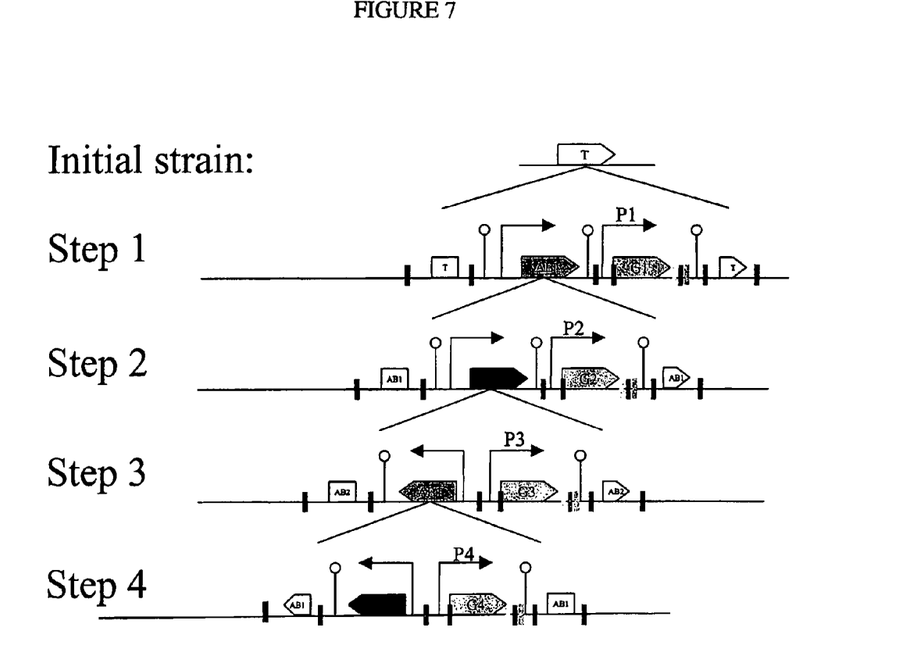
FIG. 7 demonstrates homologous recombination at target (T) sequences and antibiotic genes (AB1 and AB2) when using pStep1-4t vectors derived from pUC18Dt. The exemplary initial strain in this example is *E. coli*. However, the user can choose to use any combination of plasmids from the eight plasmids pStep1-4t and pStep 1-4-c as long as the vectors follow the alternating antibiotic resistance gene convention.
Figure 8:
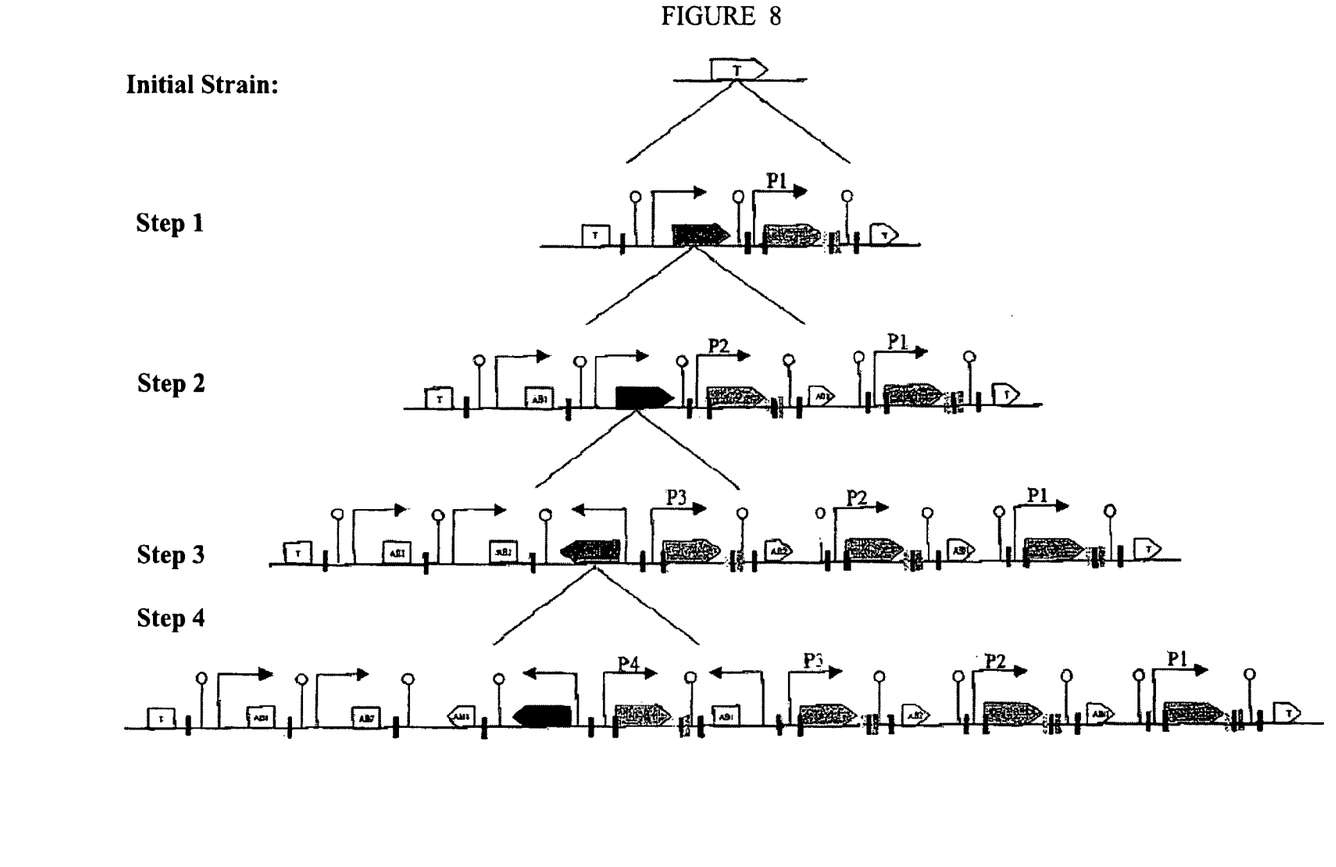
FIG. 8 shows homologous recombination of the four vectors pStep1-4t and their resulting addition of genetic elements into the host genome. The exemplary initial strain in this example is *E. coli*.

In one embodiment, once plasmid construction as defined herein is completed, the vector is linearized by restriction digest at the PstI site found in, for example, the β-lactamase on the vector backbone (AB0) and crossed into the chromosome via homologous recombination at the incorporated target sequences and selection from incorporation is performed by selecting for AB1. In some embodiments, to recursively add to an existing landing pad, the second vector in the series, which contains the two separated portions of the antibiotic resistance gene found in the first vector (e.g., AB1) and full-length expression of AB2, is crossed into the chromosome via homologous recombination at the first resistance gene (e.g., AB1), and selection by AB2 is now performed such that those host cells incorporating AB2 are selected for. The same crossing and selection based on antibiotic resistance is carried out by incorporation of the third and fourth vectors. By selectively "nesting" each antibiotic resistance gene into itself via homologous recombination (FIGS. 5 and 7), that resistance gene is effectively destroyed thereby creating a resistance switching mechanism that allows a user to continue using the same site multiple times using the same resistance genes while incorporating multiple genetic elements into the host genome (FIGS. 6 and 8). The method of recombination using the vectors as described herein exemplifies a four-fold expansion of a single landing pad with gene/promoter manipulation using simple antibiotic resistance screening.

In one embodiment, the present invention provides building blocks for synthetic genetic circuits for cellular computation, communications and signal processing. In one embodiment, the present invention provides vectors for cloning genetic elements. In some embodiments, the vectors for cloning are derived from vectors containing a replicon from the pMB1 plasmid or containing a ColEI replicon. In some embodiments, the present invention provides vectors for incorporation into a host cell genome. In some embodiments, the host cell can be prokaryotic or eukaryotic. In some embodiments, the host cell is a bacterial cell. In other embodiments, the host cell is a plant, yeast, fungal, mammalian or other vertebrate cell. In one embodiment, the vectors of the present invention utilize multiple promoter and/or enhancer sequences and termination sequences with multiple genes of interest that are incorporated into the host cell genome. In some embodiments, the promoters are useful for gene expression in bacterial systems (e.g., plac, ptac, etc.) In some embodiments, the promoter and enhancer regions are useful for eukaryotic expression (e.g., pCMV, pCaMV, pRSV, pSV40, etc.). In some embodiments, a vector of the present invention comprises target genetic sequences from the host cell, such that recombination between the host cell and a vector of the present invention can occur. In some embodiments, vectors of the present invention comprise antibiotic resistance genes, such that one resistance gene is functional and the other is non-functional and furnished in two parts, and the resistance genes are different one from the other. In some embodiments, the vectors of the present invention comprise restriction enzyme sites for incorporation of a gene of interest and associated sequences such as promoter/enhancer, and termination sequences for expression of the gene in the target host cell. In some embodiments, the vectors of the present invention can be alternatively incorporated into a host cell genome based on 1) homologous recombination via a target sequence, and 2) subsequent alternate recombination via two different antibiotic resistance gene sequences as described herein.

In one embodiment, the present invention provides for methods of incorporation of genetic material into a host cell. In some embodiments, the methods of the present invention comprise transforming a bacterial cell with the vectors as described herein. In some embodiments, one vector comprises host cell target sequences, an antibiotic resistance gene, and a gene of interest for incorporation into a host cell via homologous recombination. In some embodiments, the vector further comprises sequences that can be used to screen for incorporation of the vector into the host genome via sequencing or PCR. In some embodiments, the methods of the present invention provide for further incorporation of additional genetic elements into a host genome via homologous recombination of, for example, the second, third, fourth, etc. vectors into existing antibiotic resistance gene sequences introduced by previously incorporated vectors. It is contemplated that methods of the present invention provide for multiple insertions of genetic material into the same host using the vectors of the present invention.

In one embodiment, the present invention provides kits for practicing the methods of the present invention. In some embodiments, the kits contain any one or more components used in (e.g., necessary or sufficient for) the methods described herein, provided to an investigator in a box, bag, or other shipping means. In some embodiments, the kits of the present invention comprise two vectors. In some embodiments, the kit vectors contain a replicon from the pMB1 plasmid or contain a ColEI replicon. In some embodiments, the vectors further comprise a multiple cloning site. In some embodiments, the vectors contain a β-lactamase gene with a unique PstI site. In some embodiments, the multiple cloning site from one vector contains restriction enzyme sites that differ in order to the multiple cloning site of the second vector. In some embodiments, the kit further contains instructions for using the vectors in creating vectors for incorporating genetic elements into a host cell genome. In some embodiments, the kits further comprise reagents, buffers, enzymes (e.g., ligase, polymerase, restriction enzymes), and the like necessary for practicing the methods of the present invention. A kit of the present invention further provides host cells, solid surfaces, containers, and the like sufficient for, necessary for, or useful for shipping, storing, and practicing the methods of the present invention. It is contemplated that a kit comprises multiple components that are potentially stored at different temperatures, light conditions, etc. depending on the requirements of each component. For example, a skilled artisan will appreciate that enzymes require potentially different storage conditions that nucleic acid vectors, or buffers and reagents, and that the differential storage of such components does not change the intent of all the components that work together to create the vectors and/or practice the methods of the present invention.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for creating a synthetic genetic circuit comprising:
   a) providing:
      i) a host cell,
      ii) a first vector wherein said first vector comprises a antibiotic resistance sequence and wherein said vector is stably integrated into said host cell genome,
      iii) a second vector comprising a different antibiotic resistance sequence, genetic elements of interest, and first and second homologous sequence that are each homologous to a portion of said antibiotic resistance sequence in said first vector, wherein said first homologous sequence is located 3' of said different antibiotic resistance sequence and said genetic elements of interest, and said second homologous sequence is located 5' of said different antibiotic resistance sequence and said genetic elements of interest, and
      iv) a third vector comprising: i) an additional antibiotic resistance sequence that is not the same as said different antibiotic resistance sequence on said second vector; ii) genetic elements of interest, and iii) third and fourth homologous sequences that are each homologous to a portion of said different antibiotic resistance sequence in said second vector, wherein said third homologous sequence is located 3' of said additional antibiotic resistance sequence and said genetic elements of interest, and said fourth homologous sequence is located 5' of said additional antibiotic resistance sequence and said genetic elements of interest,
   b) applying said second vector to said host cell such that recombination occurs between said antibiotic resistance sequence in said first vector and said first and second homologous sequences thereby causing insertion of said different antibiotic resistance sequence and said genetic elements of interest at a location within said antibiotic resistance sequence of said host cell's genome which destroys the function of said antibiotic resistance sequence, and
   c) applying said third vector to said host cell such that recombination occurs between said different antibiotic resistance sequence in said second vector and said third and fourth homologous sequences thereby causing insertion of said additional antibiotic resistance sequence and said genetic elements of interest at a location within said different antibiotic resistance sequence of said host cell's genome which destroys the function of said different antibiotic resistance sequence,
wherein said genetic elements of interest comprise first and second terminators, thereby generating a synthetic genetic circuit.

* * * * *